United States Patent [19]
Fischer

[11] Patent Number: 6,096,673
[45] Date of Patent: Aug. 1, 2000

[54] CATALYST RECOVERY IN THE PRODUCTION OF 2,5-DIHYDROFURAN BY ISOMERIZATION OF VINYL OXIRANE

[75] Inventor: Martin Fischer, Ludwigshafen, Germany

[73] Assignee: BASF Aktiengesellschaft, Ludwigshafen, Germany

[21] Appl. No.: 09/066,478

[22] PCT Filed: Oct. 17, 1996

[86] PCT No.: PCT/EP96/04504

§ 371 Date: Apr. 21, 1998

§ 102(e) Date: Apr. 21, 1998

[87] PCT Pub. No.: WO97/15392

PCT Pub. Date: May 1, 1997

[30] Foreign Application Priority Data

Oct. 23, 1995 [DE] Germany .......................... 195 39 331

[51] Int. Cl.⁷ .............................. B01J 20/34; B01J 38/48; B01J 38/68; B01J 38/56; B01J 38/54
[52] U.S. Cl. ............................. 502/22; 549/507; 502/24; 502/31; 502/32; 502/155; 502/164; 203/45; 203/46
[58] Field of Search .................... 502/22, 24, 31, 502/32, 155, 164; 549/507; 203/45, 46

[56] References Cited

U.S. PATENT DOCUMENTS

| | | | |
|---|---|---|---|
| 5,034,545 | 7/1991 | Fischer | 549/507 |
| 5,082,956 | 1/1992 | Monnier et al. | 549/507 |
| 5,238,889 | 8/1993 | Falling et al. | 502/24 |
| 5,315,019 | 5/1994 | Phillips et al. | 549/507 |
| 5,466,832 | 11/1995 | Tustin | 549/507 |
| 5,591,874 | 1/1997 | Puckette et al. | 549/507 |
| 5,627,291 | 5/1997 | Fischer | 549/507 |
| 5,693,833 | 12/1997 | Falling et al. | 549/507 |

FOREIGN PATENT DOCUMENTS 412366  7/1990  European Pat. Off. .

*Primary Examiner*—Steven Bos
*Attorney, Agent, or Firm*—John H. Shurtleff

[57] ABSTRACT

An improved process is provided for the recovery of catalyst components from oligomeric impurities which are formed during the industrial preparation of 2,5-dihydrofuran by the catalytic isomerization of vinyl oxirane followed by an essential separation of the oligomeric by-products which otherwise cause deactivation of the catalyst. The catalyst components consist essentially of (a) an onium iodide and (b) a Lewis acid selected from the group consisting of the chloride, bromide or iodide of the metals zinc, tin, cobalt and bismuth, preferably zinc, where the catalyst optionally includes a donor ligand. This separation is carried out by the steps of extracting the initial product mixture containing zinc, cobalt or bismuth halides as Lewis acids with hydrocarbons or chlorinated hydrocarbons containing from 5 to 14 carbon atoms in order to form two separate phases on standing, separating off the extraction solvent phase which contains the dissolved catalyst and then recovering the separated catalyst by distilling off the extraction solvent. The recovery of tin iodide requires the presence of a special onium halide component such as phosphazenium or phosphazanium halides, preferably the iodides, having a high molecular weight and especially those which contain from 16 to 72 carbon atoms while remaining soluble in the extracting agent.

6 Claims, No Drawings

CATALYST RECOVERY IN THE PRODUCTION OF 2,5-DIHYDROFURAN BY ISOMERIZATION OF VINYL OXIRANE

DESCRIPTION

The invention relates to a process for the separation of oligomers of vinyl oxirane from an isomerization catalyst, in order to recover the catalyst for the isomerization of vinyl oxirane to 2,5-dihydrofuran, essentially comprising an onium iodide, a halide of zinc, tin, cobalt, or bismuth, and optionally a donor ligand, the catalyst contaminated with oligomers being mixed with a non-polar hydrocarbon extracting agent or chlorinated hydrocarbon extracting agent, the phases formed being separated and the extracting agent then being removed, by distillation, from the phase containing the catalyst. The catalyst can then be recycled to the isomerization reaction.

The isomerization of vinyl oxirane to 2,5-dihydrofuran is described in numerous patent specifications, eg U.S. Pat. No. 5,082,956, EP 0,412,366, WO 93/10111, and DE-A 4,424,219.

During isomerization, oligomeric by-products are formed which accumulate in the reaction mixture when the product dihydrofuran is continuously separated. It is therefore necessary to remove part of the catalystloligomer mixture in order not to exceed a specified maximum concentration of oligomers in the reaction mixture. Since the catalyst removed cannot be discarded for economical reasons, it must be recovered from the mixture removed in a form making it possible to recycle it to the isomerization phase without loss of activity.

With this aim in view U.S. Pat. No. 5,238,889 describes the separation of oligomeric byproducts formed during isomerization of vinyl oxirane to 2,5-dihydrofuran catalyzed using tetraalkylphosphonium iodides and triphenyltin iodide or tri-n-octyltin iodide, by the addition of a non-polar solvent, separation of the oligomeric byproducts undissolved in the solvent as second phase and removal by distillation of the solvent.

A drawback of combining the isomerization with separation of byproducts as described in U.S. Pat. No. 5,238,889, on an industrial scale, is the use of the said expensive organotin iodides, which are not available in gross quantities, as catalyst components.

Another disadvantage is that organotin halides are readily decomposed by water or other protic reactants. Thus there is the danger of traces of water in the vinyl oxirane used for the isomerization leading to deactivation of the catalyst as a result of the reactions:

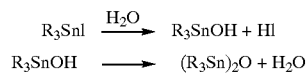

Two equivalents of the organotin iodide are here converted by one equivalent of water to form a catalytically inactive organotin' oxide.

As little as 0.,1% of water in the vinyl oxirane used for the isomerization involves the risk of economically unacceptable losses of organotin compound.

Other suitable Lewis acids for the isomerization of vinyl oxirane to 2,5-dihydrofuran are zinc halides (EP 412,366 and WO 93/10111), which are available in industrial quantities at low cost. When use is made of the process described irk U.S. Pat. No. 5,238,889 for the deposition of 6ligomeric by-products by the addition of a non-polar solvent to a catalyst mixture comprising an onium iodide and zinc chloride, bromide, or iodide it would be expected that the zinc halide would accumulate in the polar oligomer phase on account of its salt-like properties, particularly in consideration of the fact that zinc halides do not dissolve in hydrocarbons. Surprisingly the very reverse is true:

The zinc salt is concentrated together with the onium iodide in the non-polar phase, so that the oligomers can be depleted with out appreciable losses of catalyst.

Accordingly, the invention relates to a process for the separation of a catalyst from a mixture containing oligomers of vinyl oxirane, as is formed during isomerization to 2,5-dihydrofuran and from which virtually all of the low boilers have been removed, by distillation, in which the mixture of the oligomers with a catalyst, consisting essentially of a) an onium iodide,
b) a Lewis acid selected from the group consisting of the chloride, bromide or iodide of cobalt, bismuth, tin or zinc and
c) optionally a donor ligand
   (1) is thoroughly mixed with a hydrocarbon or chlorinated hydrocarbon containing from 5 to 14 carbon atoms,
   (2) the phase containing the catalyst is separated from the resulting 2 phases and
   (3) the catalyst is isolated by distilling off the solvent.

The separating process can be carried out continuously or batchwise and integrated in the isomerization process. The isomerization of vinyl oxirane is carried out as described in U.S. Pat. No. 5,238,889. This patent is included herein by reference, also in respect of the description of the onium halides, and the statements therein should be regarded as forming part of the present description except for the other type of Lewis acid (b) used.

Accordingly the hydrocarbon extracting agent or chlorinated hydrocarbon extracting agent containing from 5 to 14, preferably from 8 to 12, C atoms includes straight-chain or branched-chain, acyclic or cyclic compounds. Specific examples of acyclic extracting agents are pentane, hexane, heptane, octane, nonane, decane, mixed decanes, mixed heptanes, mixed octanes, or isooctane.

Examples of cyclic hydrocarbon extracting agents are primarily cycloalkanes containing from 6 to 12 C atoms. Specific examples are: cyclohexane, cyclooctane, and cyclododecane, and also decalin.

Preferred examples of suitable chlorinated hydrocarbons are monochlorinated compounds containing from 8 to 12 C atoms.

Suitable onium compounds (a) are all of the compounds defined in U.S. Pat. No. 5,238,889, but especially those of the formula

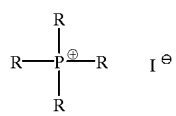

in which R denotes a hydrocarbon radical containing from 4 to 8 C atoms.

Suitable catalyst components (a) are phosphazenium or phosphazanium iodides containing from,60 to 144 C atoms over and above the onium compounds described in U.S. Pat. No. 5,238,889, selected from the group consisting of tetraalkylammonium and/or tetraarylammonium iodides and tetraalkylphosphonium and/or tetraarylphosphonium iodides containing from 16 to 72 C atoms and the individual compounds cited in said reference, provided these are at least 10% soluble in the extracting agents to be used in the present invention, at room temperature or, optionally at elevated temperature. Phosphazenium iodides are particularly suitable. These phosphazenium iodides are selected from the group consisting of the compounds defined in DE-A 4,424,219 (U.S. Pat. No. 5,627,291, issued May 6, 1997) of the formula

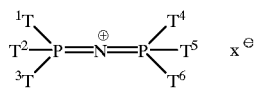

in which the radicals $T^1$ to $T^6$ have the meanings stated in DE-A 4,424,219 and $x^{63}$ denotes a counter-anion.

Those compounds are particularly suitable, in which T1 to T6 denote phenyl radicals which are substituted by a total of from 6 to 18 low molecular weight alkyl radicals.

The Lewis acids b) used in the invention are the chlorides, bromides or iodides of cobalt, tin, bismuth, or zinc or mixtures of these compounds. Of these, zinc iodide is preferred.

To achieve good selectivity of the isomerization of vinyl oxirane toward 2,5-dihydrofuran the Lewis activity of, eg, the zinc halide is diminished by a weakly basic donor ligand c). Suitable compounds are the compounds described in DE-A 4,424,219. Tertiary amides such as N,N-dimethyloctane carboxamide, N,N-dimethylbutyramide, lactams such as N-cyclohexylpyrrolidone, N-octylpyrrolidone, N-octylcaprolactam, or ureas such as tetrabutylurea, tetraoctylurea, N,N-dioctylethylene urea or N,N-dioctylpropylene urea are particularly noteworthy examples where the amides, lactams, or ureas should contain from 16 to 54 C atoms.

Other particularly suitable donor ligands are trialkylphosphane oxide or triarylphosphane oxides such as tributylphosphane oxide, trioctylphosphane oxide, or triphenylphosphane oxide and also phosphoric triamides such as hexabutyl or hexaoctylphosphoric triamide.

Since, based on vinyl oxirane to be isomerized, the catalyst component a) is usually employed in amounts of from 0.01 to 5 wt % and preferably from 0.5 to 1 wt % and the catalyst component b) in amounts of from 0.0001 to 0.5 wt % and preferably from 0.001 to 0.2 wt %, the ratio of component a) to component b) in the mixture is from 1:0.001 to 1:0.1 and preferably from 1:0.01 to 1:0.1. The content of the donor ligand c) in the catalyst mixture is usually from 0.01 to 30 wt % and preferably from 0.1 to 10 wt %.

The content of the entire catalyst mixture in the mixture to be separated by the method of the invention (i.e., following the removal of virtually all of the low boilers such as dihydrofuran, vinyl oxirane, and crotonaldehyde) with the oligomers depends on the amount of the catalyst mixture used in the isomerization and the extent of removal of the oligomers. It is usually from 20 to 90 wt % and preferably from 50 to 80 wt %, based on the entire catalyst/oligomer mixture.

The catalyst recovery process of the invention can be carried out batchwise, semi-continuously, or continuously. When the process is carried out batchwise the volatile components of the isomerization reaction mixture are removed, by distillation, and he extracting solvent is added to the residue, the components are mixed thoroughly and, following separation of the phases, the catalyst mixture is isolated by distilling off the extracting agent. In this case all or virtually all of the volatile components should be removed from the catalystloligomer mixture, as otherwise a portion of the oligomers will be solubilized in the extracting agent. The amount of the volatile components of the catalyst system is usually from 5 to 30 wt % of the catalyst/oligomer mixture to be extracted. The extraction of the oligomer phase can be repeated, if necessary, and the extracts combined by evaporative concentration for purification purposes. The catalyst system is obtained as a molten liquid which can be recycled to the isomerization process without further purification. Small amounts of oligomer still remaining in the catalyst system have no undesirable effect when reused in the isomerization.

The oligomer can be isolated as by-product or it can be discarded. The catalyst components may, if desired, be isolated by crystallization from the molten catalyst mixture, but direct recycling is preferred.

The extraction process of the invention is usually carried out at slightly elevated temperature to ensure good solubility of the catalyst in the solvent and reduced viscosity of the oligomers. However, a temperature below the boiling point of the solvent is advantageously selected in order to make it possible to operate at atmospheric pressure. This means that the extraction is usually carried out at temperatures ranging from 400 to 125° C.

However, the extraction is usually carried out semi-continuously or, preferably, continuously by standard prior art procedures, eg as specified in T. C. Lo, M. H. I. Baird, C. Hanson, Handbook of Solvent Extraction, Reprint Edition, Krieger Publishing Company, Malabar, Fla. U.S.A. 1991. Typical counter-current extraction systems are, for example, mixer/settlers, sieve tray columns, stirred columns such as Kuhni columns or rotating disk columns or columns incorporating mechanically agitated trays. When the process is carried out continuously a portion of the catalyst/oligomer mixture is constantly removed from the reactor and the volatile components are continuously removed, by distillation. The concentrated mixture is then continuously fed to multi-stage extraction means countercurrently to the extracting agents. The catalyst mixture is then obtained from the extract by evaporation.

The amount of solvent used for the extraction depends on the type of catalyst system used, its content in the oligomer mixture and on the type of solvent used and also on the manner in which the extraction is carried out. However, the ratio of solvent to catalyst/oligomer mixture is usually set at from 10:1 to 0.1:1.

EXAMPLE 1 (separation of the catalyst)

In an oil-heated stirred flask a mixture of 85.6 g of tri-noctyl(n-octadecyl)phos-phonium iodide, 3.8 g of zinc iodide, and 11.5 g of N-cyclohexylpyrrolidone is heated to 100° C. with stirring under a blanket of nitrogen. 1840 g of vinyl oxirane are pumped in by means of a flow control pump at a constant rate of 40 g/h. The 2,5-dihydrofuran formed is continuously removed, by distillation, together with residues of unconverted vinyl oxirane and traces of crotonaldehyde. When the feed is complete the pressure is gradually reduced to 10 mbar in order to remove the low boilers, by distillation, as far as possible. 7

In all, 1,766 g of distillate are isolated which consists of 83.5% of 2,5-dihydrofuran, 15% of vinyl oxirane and 1.52 o of crotonaldehyde. The selectivity toward 2,5-dihydrofuran is 93.6% at a conversion of 85.6%.

The bottoms, which are viscous at room temperature, are mixed with 350 mL of n-octane and heated to 80° C. with stirring. On termination of stirring, the bottom phase is separated and thoroughly mixed with a further 250 mL of n-octane at 80° C. and the bottom phase is subsequently again separated.

Following evaporation of the bottom phase in a rotary evaporator at 80° C./14 mbar 40 g of bottoms remain. This residue contains 1.3% of iodine and 0.03% of zinc. It can be concluded from these analytical data that 97% of the iodine and 98.5% of the zinc have remained in the two octane phases.

Following combination of the two octane phases, these are evaporated off in a rotary evaporator at a bath temperature of 80° C. and a pressure of 14 mbar, 135 g of residue remaining, which solidifies at room temperature.

EXAMPLE 1a (catalyst feedback)

The evaporation residues from the octane phases of Example 1 are heated to 125° C. With stirring, 800 g of vinyl oxirane are pumped in continuously at a rate of 35 g/h and 2,5-dihydrofuran is distilled off together with unconverted vinyl oxirane. When the feed is complete, the low boilers are substantially removed, by distillation, by reduction of the pressure to 10 mbar. There are obtained 747.2 g of distillate having the following composition: 82% of 2,5-dihydrofuran, 16.5% of vinyl oxirane, and 1.5% of crotonaldehyde.

EXAMPLE 2

A mixture of 42.8 g of tri-n-octyl(-n-octadecyl) phosphonium iodide, 1.92 g of zinc iodide, and 33 g of tri-n-octylphosphane oxide is heated to 125° C. with stirring. 1442 g of vinyl oxirane are pumped in at a rate of 20 gal. The 2,5-dihydrofuran formed by isomerization is continuously removed, by distillation, together with uncornverted vinyl oxirane and traces of crotonaldehyde. When the feed is complete, the pressure is gradually reduced to 10 mbar in order to remove the low boilers, by distillation, as far as possible.

In all, there are obtained 1,370 g of distillate having the following composition: 85% of 2,5-dihydrofuran, 1.1% of crotonaldehyde, and 13.9% of vinyl oxirane. This gives, by calculation, a selectivity of 93% and a conversion of 86.8%.

The bottoms are extracted as described in Example 1 at 80° C. once with 250 mL and once with 172 mL of n-octane. Following evaporation of octane residues at 80° C./16 mbar there remain 22 g of a residue comprising oligomeric vinyl oxirane, which contains 0.70% of iodine and 0.015 o of zinc. It can be concluded from these data that 98% of the iodine and 99.2% of the zinc have remained in the two octane phases.

The octane phases evaporated off lead to an isomerization catalyst which shows unchanged activity and selectivity under the conditions described above and can be recycled to the isomerization reaction after further purification.

What is claimed is:

1. In a process for the production of 2,5-dihydrofuran by the isomerization of vinyl oxirane in the presence of an isomerization catalyst, the improvement for separating and removing oligomeric by-products for recovery of the catalyst which comprises:

carrying out the isomerization with a catalyst consisting essentially of
   a) an onium iodide,
   b) a Lewis acid which is at least one halide selected from the group consisting of the chlorides, bromides and iodides of zinc, cobalt and bismuth, and
   c) optionally, a donor ligand
   to obtain an initial reaction product mixture of the catalyst together with said dihydrofuran product and the oligomeric by-product from which substantially all lower boiling components are removed by distillation, and then recovering the catalyst by the steps of
      1) thoroughly mixing said initial product mixture with an extraction solvent selected from the group consisting of hydrocarbons and chlorinated hydrocarbons containing from 5 to 14 carbon atoms and permitting the mixture to stand and form two phases;
      2) separating the extraction solvent phase which contains the dissolved catalyst, and
      3) isolating and recovering the separated catalyst by distilling off said extraction solvent.

2. A process as claimed in claim 1, wherein said extraction solvent is an alkane containing from 5 to 14 carbon atoms.

3. A process as claimed in claim 1, wherein said extraction solvent is a hydrocarbon containing from 8 to 12 carbon atoms.

4. A process as claimed in claim 1, wherein the catalyst being extracted consists essentially of a phosphonium iodide, zinc iodide and a ligand donor selected from the group consisting of straight-chain amides, cyclic N-substituted amides and trialkylphosphane oxides.

5. A process as claimed in claim 1, wherein the onium component a) of the catalyst is selected from the group consisting of phosphazenium and phosphazanium iodides, containing from 60 to 144 carbon atoms while remaining soluble in the extracting agent.

6. A process as claimed in claim 5, wherein the onium component a) of the catalyst is a phosphazenium iodide.

* * * * *